(12) United States Patent
Laurent

(10) Patent No.: US 6,565,791 B1
(45) Date of Patent: May 20, 2003

(54) METHOD AND APPARATUS FOR TREATING THE INSIDE SURFACE OF PLASTIC BOTTLES IN A PLASMA ENHANCED PROCESS

(75) Inventor: Jacques Laurent, Blonay (CH)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 09/509,470

(22) PCT Filed: Sep. 28, 1998

(86) PCT No.: PCT/IB98/01506
§ 371 (c)(1), (2), (4) Date: May 19, 2000

(87) PCT Pub. No.: WO99/17334
PCT Pub. Date: Apr. 8, 1999

(30) Foreign Application Priority Data

Sep. 30, 1997 (CH) ............................................ 2289/97

(51) Int. Cl.⁷ ............................. H05B 6/00; B29C 35/08
(52) U.S. Cl. ..................... 264/455; 264/524; 264/129; 425/174; 425/174.4; 425/529; 425/404
(58) Field of Search ................................. 264/455, 524, 264/129; 425/174, 174.4, 529, 404

(56) References Cited

U.S. PATENT DOCUMENTS

| | | | |
|---|---|---|---|
| 4,265,730 A | * 5/1981 | Hirose et al. | 118/723 AN |
| 5,378,510 A | 1/1995 | Thomas et al. | |
| 5,521,351 A | 5/1996 | Mahoney | |
| 5,531,060 A | * 7/1996 | Fayet et al. | 264/525 |
| 6,117,243 A | * 9/2000 | Walther | 118/712 |
| 6,198,224 B1 | * 3/2001 | Spitzl et al. | 118/723 MW |

FOREIGN PATENT DOCUMENTS

| | | |
|---|---|---|
| DE | 3632748 C2 | 4/1989 |
| DE | 43 18 086 A1 | 12/1994 |
| DE | 195 02 103 A1 | 8/1995 |
| DE | 196 00 223 A1 | 7/1997 |
| EP | 0 773 167 A1 | 5/1997 |

OTHER PUBLICATIONS

XP-002067698.
Patent Abstract for Japan, JP08053117-A.
WO 95/22413, Publication Date: Aug. 24, 1995, Hollow Containers with Inert or Impermeable Inner Surface Through Plasma–Assisted Surface Reaction or On–Surface Polymerization.

* cited by examiner

*Primary Examiner*—Suzanne E. McDowell
(74) *Attorney, Agent, or Firm*—Rankin, Hill, Porter & Clark LLP

(57) ABSTRACT

The apparatus for treating the inside surface of a bottle (1) in a plasma enhanced process comprises a vacuum chamber (2), a microwave confinement (3) with a microwave generator (4), evacuation means and gas feed means (5). The microwave confinement (3) is substantially cylindrical and adapted to the shape of at least the body portion of the bottle (1) to be treated as closely as possible. The microwaves are coupled into the microwave confinement (3) form the bottom side of the bottle (1) and the microwave confinement is excited in a TM mode of resonance. The inventive apparatus is very compact and very simple. It can be integrated into a stretch-blow-moulding apparatus or into a filling apparatus. For upscaling, a plurality of one-bottle apparatuses is arranged in a row or in a matrix and all the one-bottle apparatuses are connected to a net of energy, vacuum and gas supply lines. Each of the one-bottle apparatuses may have its own vacuum chamber or a plurality of microwave confinements (3) may be arranged in one common vacuum chamber.

15 Claims, 7 Drawing Sheets

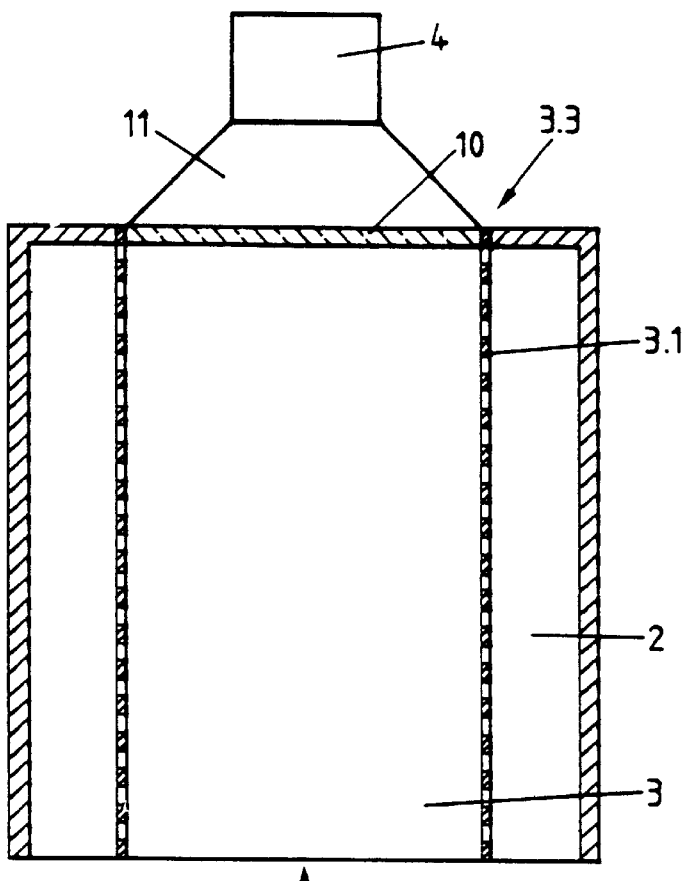
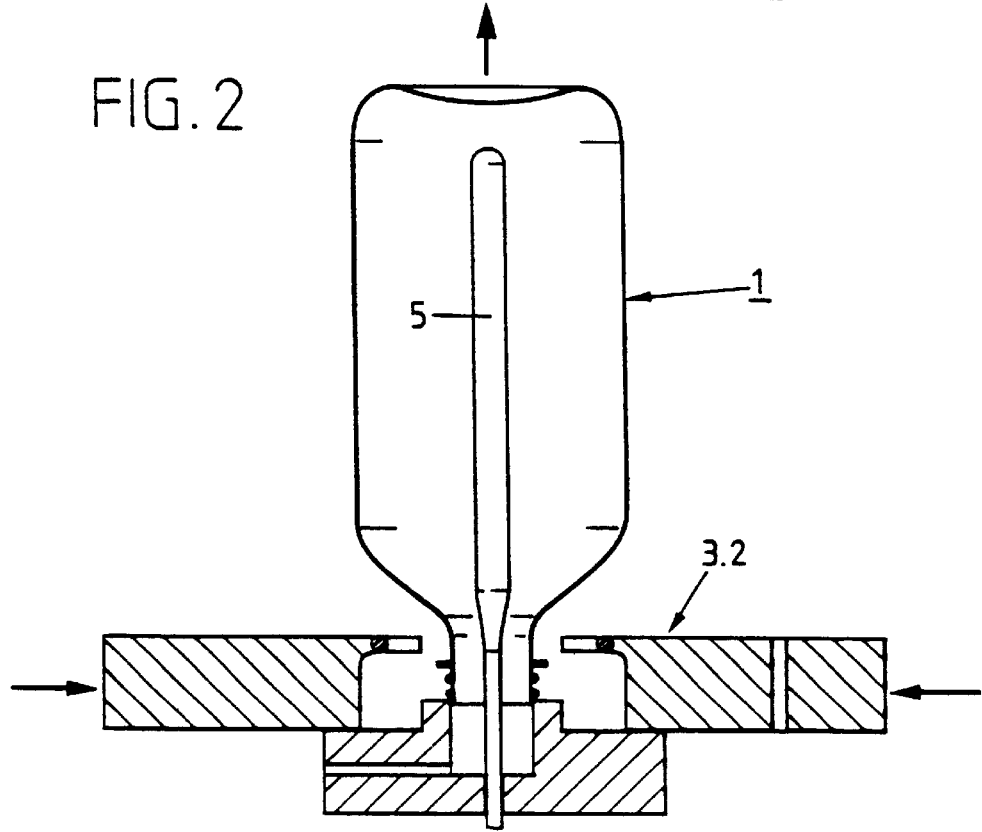
FIG. 2

METHOD AND APPARATUS FOR TREATING THE INSIDE SURFACE OF PLASTIC BOTTLES IN A PLASMA ENHANCED PROCESS

The invention lies in the field of the packaging industry and relates to a method and an apparatus according to the generic parts of the corresponding independent claims, which method and apparatus serve for treating the inside surface of plastic bottles using a plasma enhanced process.

The term plastic bottle is used in the present description for a container made of a plastic material and having a body portion in the form of an upright cylinder with a circular or a non-circular cross section, a bottom portion on the one face of the body portion and a shoulder and neck portion with a relatively narrow opening on the other face of the body portion. Such containers are in particular bottles made e.g. of polyethyleneterephthalate (PET), polypropylene (PP) or high density polyethylene (HDPE), which bottles are e.g. produced by stretch blow moulding. Such bottles, for improving their gas barrier properties, are subjected to a coating treatment for coating their inner surface with a layer of silicon oxide in a plasma enhanced chemical vapour deposition process.

Other plasma enhanced processes used for treating the inside surface of plastic bottles are e.g. sterilizing processes or processes for activating or otherwise changing the surfaces.

Plasma enhanced processes for treating the inside surface of plastic bottles as well as devices for carrying out such processes have been described e.g. in the publications J. Weichart, B. Meyer, J. Müller (Vakuum in der Praxis Nr. 1, pages 22–26, 1991), U.S. Pat. No. 5,521,351 (Wisconsin Alumni Research), JP-0853117 (Kirin Brewery), U.S. Pat. No. 5,378,510 (Polar Materials Inc.), DE-3632748 (Vereinigung zur Förderung des Instituts für Kunststoffverarbeitung in Industrie und Handwerk an der TH Aachen) and WO-95/22413 (Coca-Cola Company).

A plasma enhanced process for treating the inside of a bottle generally comprises the steps of reducing the pressure within the bottle, igniting and sustaining a plasma within the bottle by activating a suitable power source (DC, RF, HF, microwave) and flowing a suitable process gas or process gas mixture through the plasma. In most cases it is necessary to evacuate the room outside of the bottle also in order to prevent the bottle from collapsing. Advantageously the room outside the bottle is evacuated to a pressure which is approximately ten times lower than the pressure inside the bottle such preventing ignition of a plasma on the outside of the bottle.

Devices for carrying out such processes therefore comprise: a vacuum chamber, in which the bottle to be treated is positioned, means for evacuating the vacuum chamber and means for evacuating the inside of the bottle (usually two different reduced pressures), means for igniting and sustaining a plasma (e.g. generator for RF- or HF-frequency or microwave generator) and means for feeding the process gas into the bottle.

It is the object of the invention to provide a method and an apparatus for treating the inside surface of plastic bottles in a plasma enhanced process, e.g plasma enhanced chemical vapour deposition of a silicon oxide coating. Using the inventive method and apparatus is to make it possible to produce a high quality product in an economically feasible process and the inventive apparatus is to be easily upscaleable for a high capacity process.

This object is achieved by the method and apparatus as defined by the claims.

The inventive apparatus comprises a vacuum chamber and a substantially cylindrical microwave confinement to which microwaves generated by a microwave generator are coupled through one of the faces with the aid of suitable coupling means, whereby the function of the microwave confinement and of the vacuum chamber may be taken over partially or fully by the same apparatus part. It further comprises evacuation means and gas feed means. The microwave confinement is adapted to the shape of at least the body portion of the bottle as closely as possible. The microwave confinement, the coupling means and the microwave generator are designed and tuned such that the microwave confinement is excited in a TM resonance mode, i.e. by a transverse magnetic wave, in which the magnetic field does not have axial components. In addition a permanent magnetic field can be generated by providing stationary magnets which magnetic field is preferably such that within the bottle to be treated electron cyclotron resonance conditions are achieved.

The inventive apparatus is very compact and very simple. For upscaling, a plurality of one-bottle apparatuses is arranged in a row or in a matrix and all the one-bottle apparatuses are connected to a net of energy, vacuum and gas supply lines. Each of the one-bottle apparatuses may have its own vacuum chamber or the plurality of microwave confinements may be arranged in one common vacuum chamber.

Exemplified embodiments of the inventive apparatus are described in connection with the following Figures. Wherein:

FIGS. 1 and 2 show the principle of an exemplified embodiment of the inventive apparatus for treating one bottle at a time in an operative or closed configuration (FIG. 1) and in an open configuration (FIG. 2);

Figure 1:
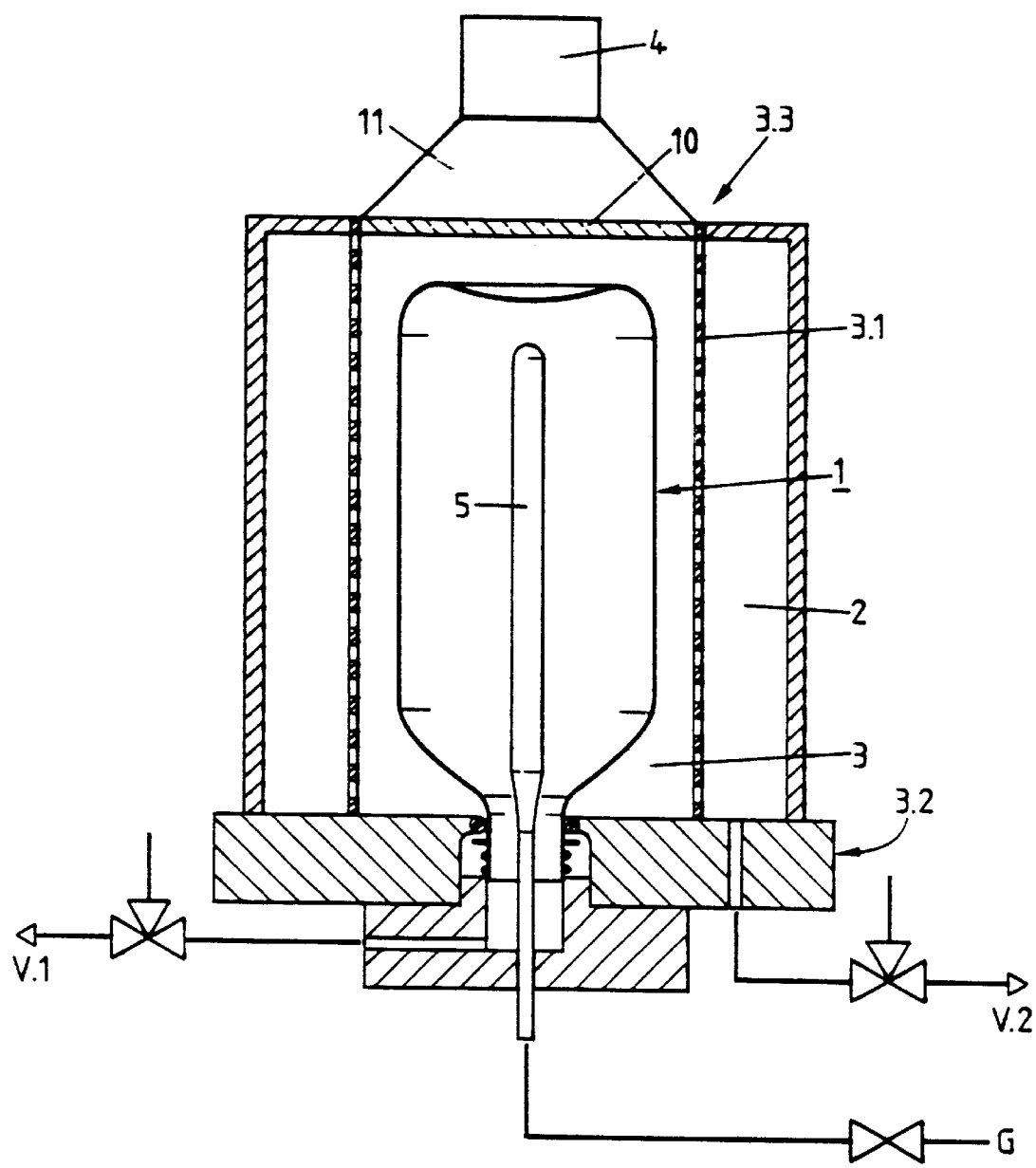

FIGS. 1 and 2 show an exemplified embodiment of the inventive apparatus for treating one bottle 1 at a time. The apparatus comprises a vacuum chamber 2 and a cylindrical microwave confinement 3 or part of a microwave confinement within the vacuum chamber and wherein the bottle 1 to be treated is positionable. It further comprises a microwave generator 4 and suitable coupling means (10/11) for exciting the microwave confinement and a gas feed tube 5 reaching through the bottle opening into the inside of the bottle and consisting of a porous or perforated material. FIG. 1 shows the apparatus in its operational or closed configuration, wherein the microwave confinement and the vacuum chamber are closed. FIG. 2 shows the apparatus in its open configuration which open configuration serves for exchanging a treated bottle with a further bottle to be treated.

The microwave confinement 3 either consists of a material which is not transparent to microwave but allows pressure equilibration between its inside and its outside (e.g. is made of a perforated metal sheet) and is positioned within the vacuum chamber 2 or it is not transparent to micro waves and vacuum tight, i.e it takes over the function of the vacuum chamber at the same time. In the embodiment according to FIGS. 1 and 2 the microwave confinement 3 comprises a perforated cylindrical part 3.1 which corresponds as closely as possible to the cylindrical body portion of the bottle 1. The cylindrical part 3.1 is closed on one side by a neck plate 3.2 which neck plate forms a wall part of the vacuum chamber 2 also and comprises means for holding the neck portion of the bottle 1 to be treated and means for sealing the inside of the bottle from the outside and carries the gas feed tube 5. The neck plate also comprises means for connecting the gas feed tube to a process gas G source, means for connecting the bottle opening to a vacuum V.1 source and means for connecting the vacuum chamber to a vacuum V.2 source.

At the face 3.3 opposite the neck plate 3.2 and facing the bottom part of the bottle to be treated microwaves generated by a microwave generator 14 are coupled into the microwave confinement, e.g. via a hollow wave guide 11 through a microwave transparent window 10 which at the same time represents the vacuum chamber wall. The window 10 is e.g. made from quartz glass or plastic.

It is possible also, to use a vacuum chamber transparent to microwaves (from quartz or plastic) and to arrange it fully or partly within the microwave confinement.

The microwave generator 4, the microwave confinement 3 and the microwave coupling means are designed and tuned for a TM mode of resonance, preferably for a $TM_{01n}$ mode wherein n is between 1 and 4. In the publications U.S. Pat. Nos. 5,311,103 and 4,777,336 devices showing such resonance are described.

For creating a stationary magnetic field inside the bottle 1 to be treated, the gas feed tube 5 may be equipped with a plurality of stationary magnets positioned either inside the tube or arranged on its outside. The gas feed tube may further comprise cooling means for cooling the gas feed tube and the magnets and keeping them at a temperature which is constant within narrow limits.

The gas feed tube may also be designed as a simple perforated tube or may be reduced to a gas feed nozzle positionable in the neck of the bottle to be treated.

For positioning a bottle 1 to be treated in the microwave confinement 3 (refer to FIG. 2), the neck plate 3.2 is removed from the cylindrical part 3.1 of the microwave confinement 3. The means for holding the bottle neck are opened. Then the bottle 1 is positioned over the gas feed tube 5 or gas feed nozzle and is secured by the neck holding means. Then the bottle is introduced into the vacuum chamber 2 and the microwave compartment 3 by moving the neck plate 3.2 towards the cylindrical part 3.1 until it forms a tight seal not only with the other wall parts of the vacuum chamber but also with the cylindrical part 3.1 of the microwave confinement.

Figure 3:
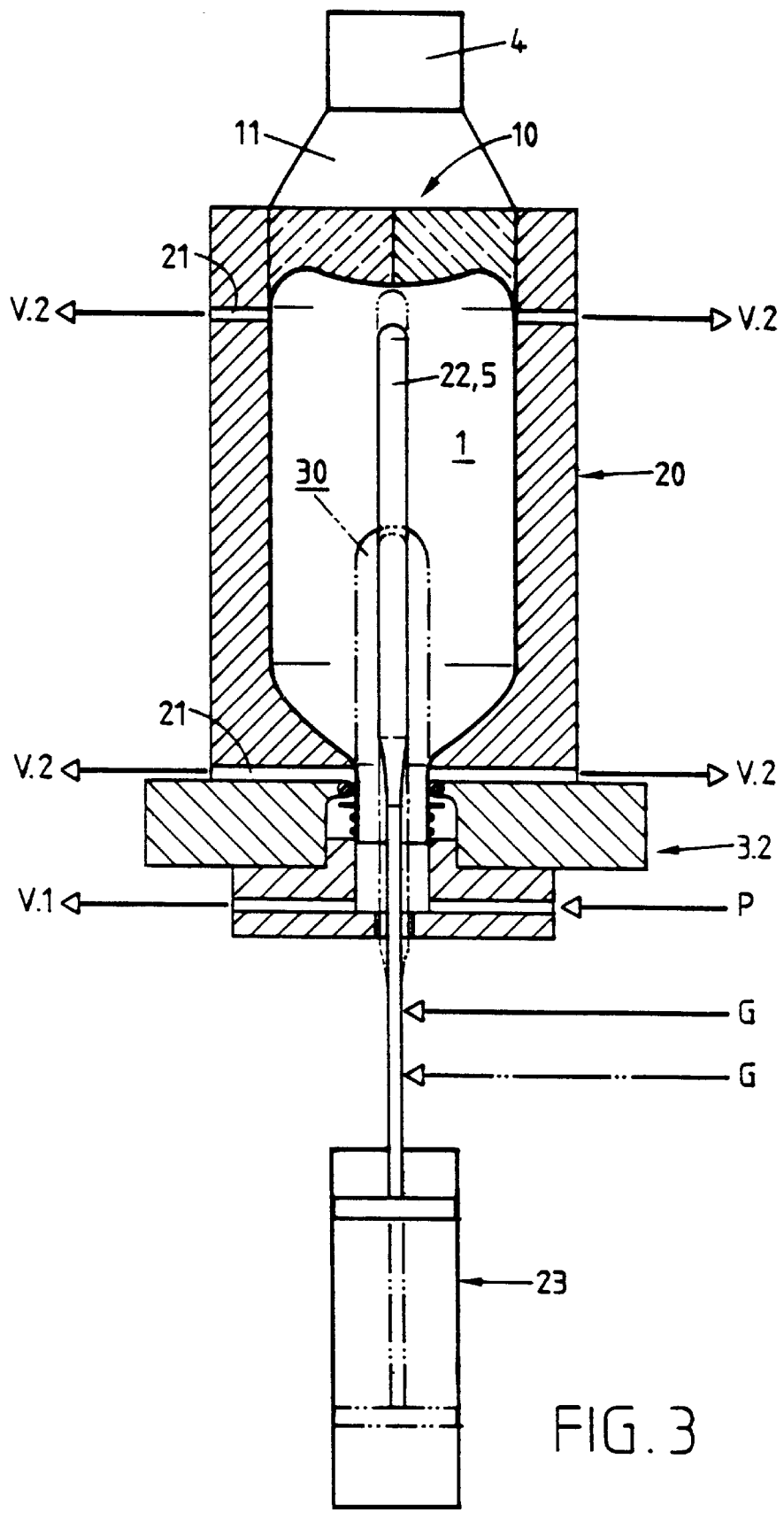
FIG. 3 shows a further embodiment of the inventive apparatus integrated in a stretch-blow-moulding apparatus, in which apparatus a bottle is stretch-blow-moulded and immediately afterwards is treated in a plasma enhanced process.

FIG. 3 shows a further exemplified embodiment of the inventive apparatus for coating one bottle 1 at a time. The apparatus is fully integrated into an apparatus for stretch-blow-moulding the bottle 1. The function of the vacuum chamber and of the microwave confinement are taken over by the cavity of the blow mould 20. For the new functions the blow mould comprises a microwave window 10, e.g. made of quartz glass to which window 10 microwaves generated by the microwave generator 4 are coupled via the wave guide 11, and at least one channel 21 through which the mould cavity can be evacuated (V.2).

The stretching rod 22 of the stretch-blow-moulding apparatus is moved to its various positions by a linear motor 23. It is hollow and made of a porous or perforated material and serves as gas feed tube 5 in the plasma enhanced process. Therefore it comprises a connection to a process gas source G.

The apparatus according to FIG. 3 is operated as follows:

A preheated bottle preform 30 (in broken lines) is positioned in the cavity of the mould 20. The stretching rod/gas feed tube 22/5 is in an initial position its distal end being positioned against the bottom part of the preform. The vacuum connections of the mould are closed.

Pressure P is applied to the inside of the preform and the stretching rod/gas feed tube 22/5 is advanced until it reaches or nearly reaches the bottom part of the mold opposite the bottle opening, such stretching the preform to approximately the axial length of the bottle to be produced.

The pressure P is then increased for blowing the preform wall and pressing it onto the inside of the mould 20.

The stretching rod/gas feed tube 22/5 is then brought into a gas feed position (distal end at a distance from the bottle bottom) and the inside of the bottle is evacuated simultaneously with the cavity of the mould, whereby the reduced pressure inside the bottle is suitable for igniting a plasma and the reduced pressure outside of the bottle is preferably too high or too low for igniting or sustaining a plasma but suitable to keep the bottle from collapsing.

The microwave generator is activated and the process gas is fed to the stretching rod/gas feed tube 22/5 and is simultaneously removed through the opening of the bottle (V.1) thereby maintaining a suitable process pressure.

After the predetermined process time, the microwave generator and the process gas are stopped and the bottle 1 and the mould cavity are vented.

The mould 20 is opened and the stretch-blow-moulded and treated bottle is removed from the mould.

Figure 4:
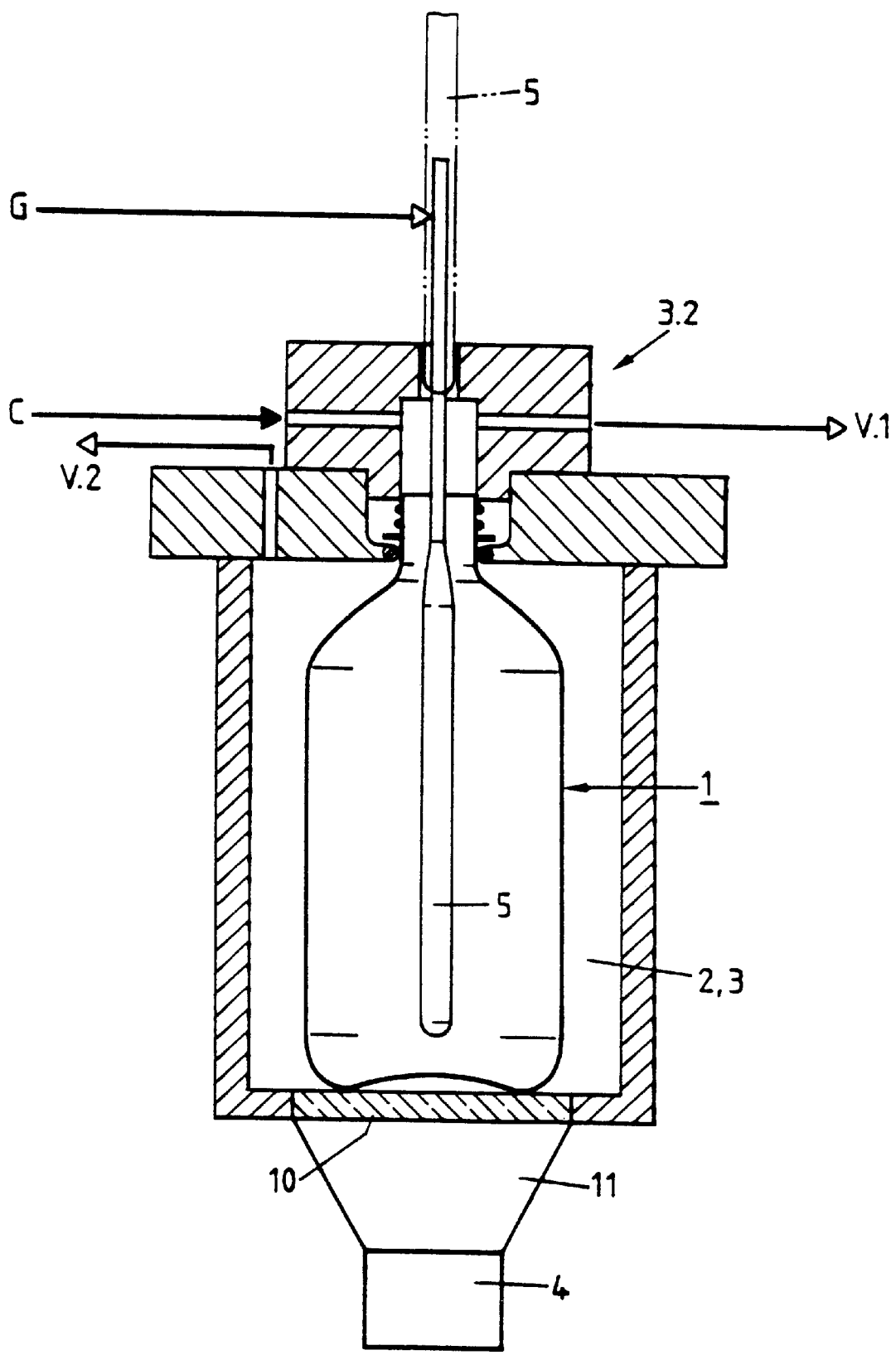
FIG. 4 shows a further embodiment of the inventive apparatus integrated in a filling apparatus, in which apparatus the bottle is filled immediately after treatment in the plasma enhanced process.

FIG. 4 shows a further exemplified embodiment of the inventive apparatus for treating one bottle 1 at a time. The apparatus corresponds substantially to the apparatus according to FIGS. 1 and 2. The function of the microwave confinement 3 is here taken over by the vacuum chamber 2. The apparatus further comprises means (not shown) for moving the gas feed tube 5 into a position outside of the bottle 1 (shown in broken lines (5)) and a connection in the neck plate 3.2 to a source of a liquid C to be filled into the treated bottle.

The apparatus according to FIG. 4 is operated as follows:

A bottle 1 is positioned in the microwave confinement/vacuum chamber. The gas feed tube 5 is brought into a gas feed position inside the bottle (distal end at a distance from the bottle bottom).

The inside of the bottle 1 is evacuated simultaneously with the vacuum chamber 2, whereby the reduced pressure inside the bottle is suitable for igniting a plasma and the reduced pressure outside of the bottle is preferably too high or too low for igniting or sustaining a plasma but suitable to keep the bottle from collapsing.

The microwave generator is activated and the process gas is fed to the gas feed tube 5 and is simultaneously removed through the opening of the bottle (V.1) thereby maintaining a suitable process pressure.

After the predetermined process time, the microwave generator and the process gas are stopped.

If necessary, the bottle is rinsed with a rinsing gas keeping a reduced pressure.

The connection to the source of liquid content C is opened and the bottle is filled with the liquid sucked into the bottle due to the vacuum.

The treated and filled bottle is sealed and removed from the microwave confinement/vacuum chamber.

The advantage of the apparatus according to FIG. 4 is not only the use of the vacuum for filling the bottle but also the filling of the bottle straight after the plasma treatment which renders the inside surface of the bottle not only e.g. coated but sterile also. Therefore, the use of an apparatus according to FIG. 4 makes a sterilizing apparatus or means for sterile transport of the treated bottles to a filling apparatus unnecessary.

It is also possible to combine the features of the apparatus according to FIG. 3 with the features of the apparatus according to FIG. 4 resulting in a stretch-blow-moulding/plasma-treating/filling apparatus combined in one and the same apparatus.

Figure 5:
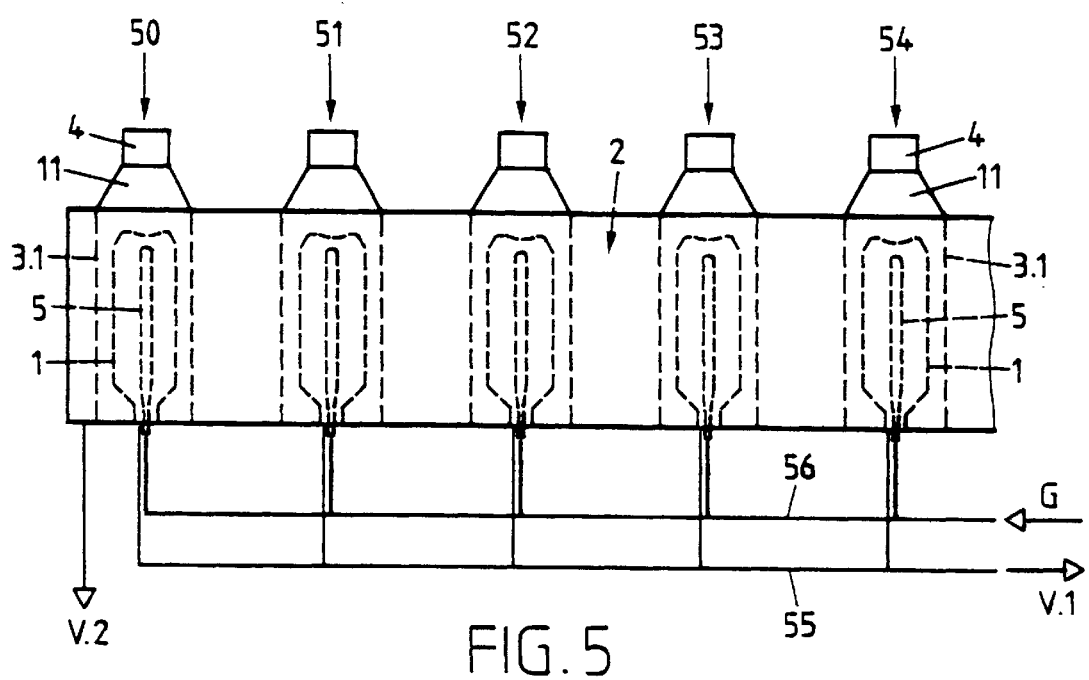
FIGS. 5 and 6 show schematic exemplified embodiments of the inventive apparatus for simultaneous treatment of a plurality of bottles in a plasma enhanced process.
Figure 6:
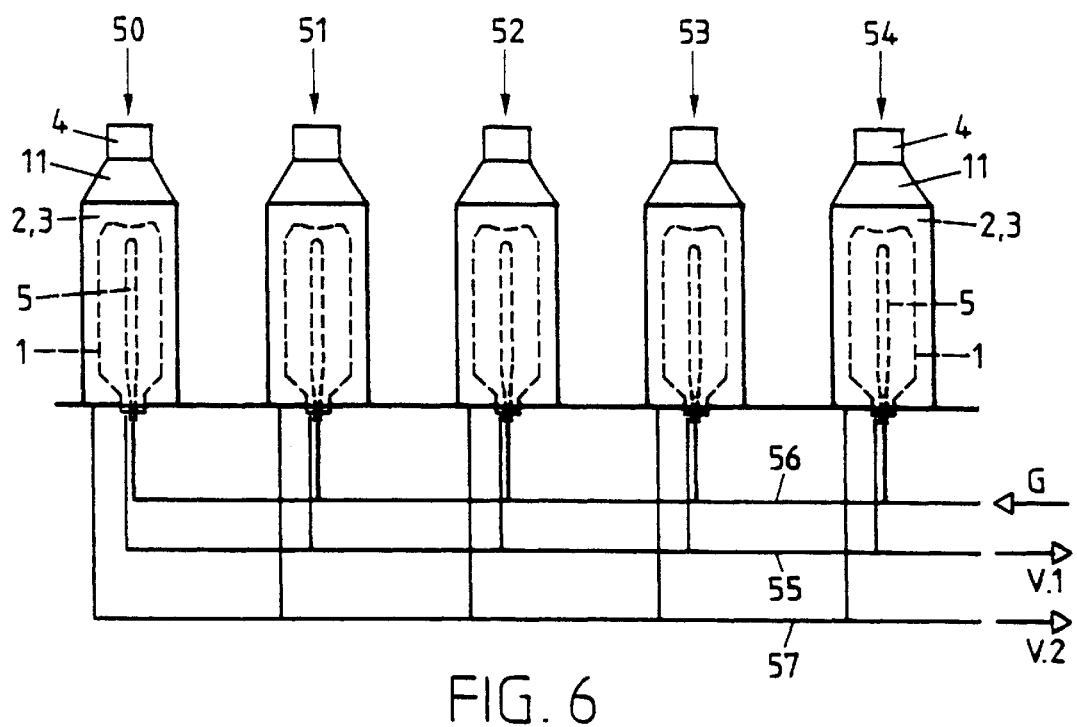

FIGS. 5 and 6 show very schematic, exemplified systems for treating a plurality of bottles at one time. The basic idea of these systems is to provide a plurality of units 50, 51, 52 . . . which substantially correspond to the apparatuses according to FIGS. 1 and 2 or according to FIG. 4, whereby the units may be arranged within a common vacuum chamber (FIG. 5) or may each comprise its own individual vacuum chamber (FIG. 6).

Each unit 50, 51, 52 . . . is connected to a net of vacuum lines 55 for evacuating the bottles and to a net of gas feed lines 56 for the process gas and if applicable to a net of vacuum lines 57 for evacuating the individual vacuum chambers and to supply lines for a liquid content to be filled into the bottles.

The units in the systems according to FIGS. 5 and 6 are arranged in a row or in a matrix and are advantageously opened and closed using one common drive. A plurality of units can also form a line or rotary system of units wherein the units are moved either continuously or by increment.

Figure 7:
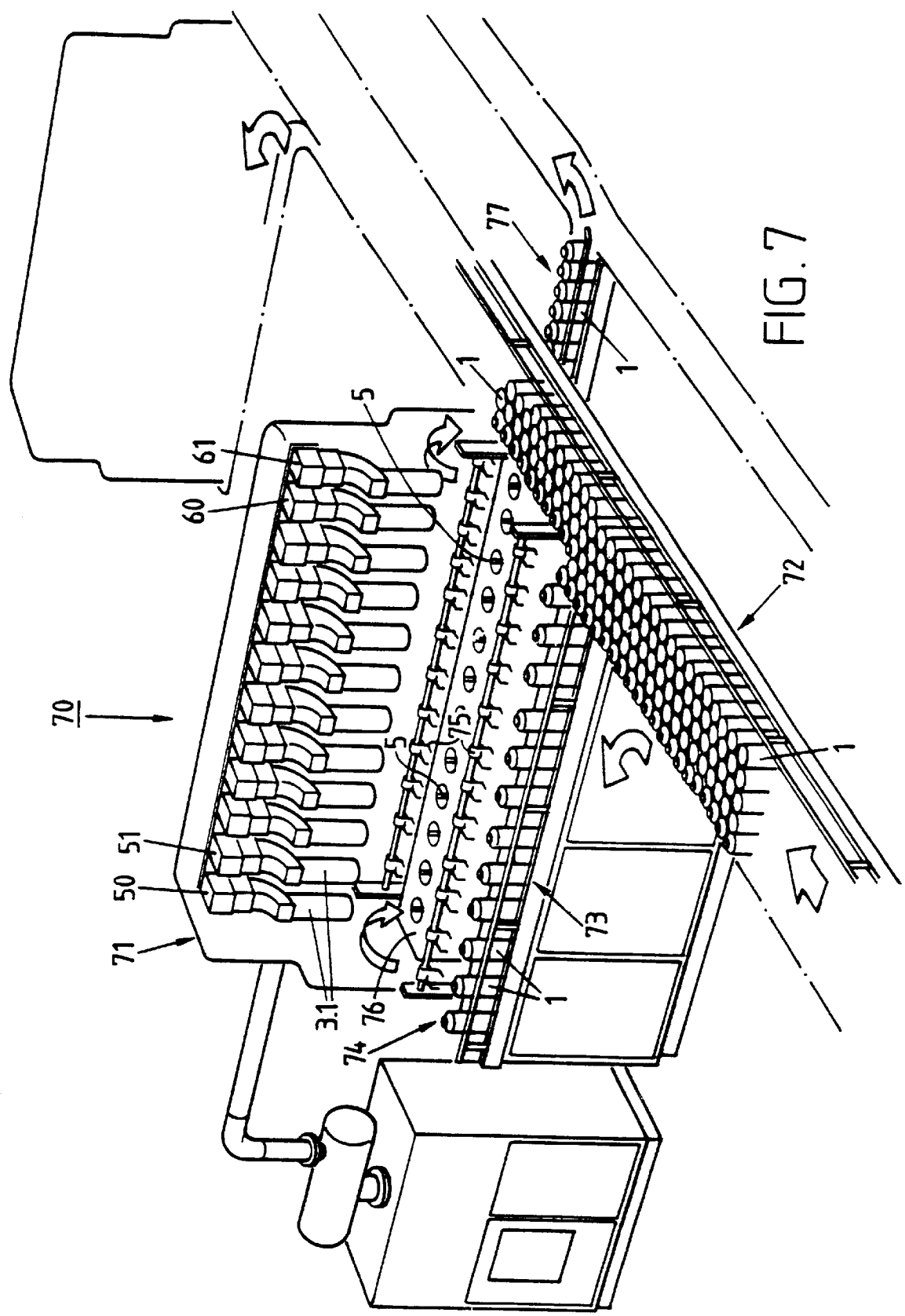
FIG. 7 shows a three dimensional representation of an embodiment of the inventive apparatus according to FIG. 5.

FIG. 7 shows with a bit more detail a system 70 according to FIG. 5, i.e. a system with a row of twelve units 50 to 61 according to FIGS. 1 and 2 arranged in a row in a common vacuum chamber 71.

The bottles to be treated are supplied to the system by a supplying conveyor 72 and a branch conveyor 73 and are arranged in a bottle row 74 parallel to the row of units. The row of bottles may be positioned in a vacuum lock chamber. For positioning the bottles of the bottle row 74 into the units 50 to 61 the vacuum chamber is opened and the bottles are gripped by a gripper row 75. They are tilted and moved above the gas feed tubes 5 which are in a position beneath the common neck plate 76. Then the gas feed tubes are raised and the vacuum chamber is closed. The bottles are then treated and after treatment are removed by opening the vacuum chamber, lowering the gas feed tubes, and tilting the bottles onto a removal conveyor 77.

Figure 8:
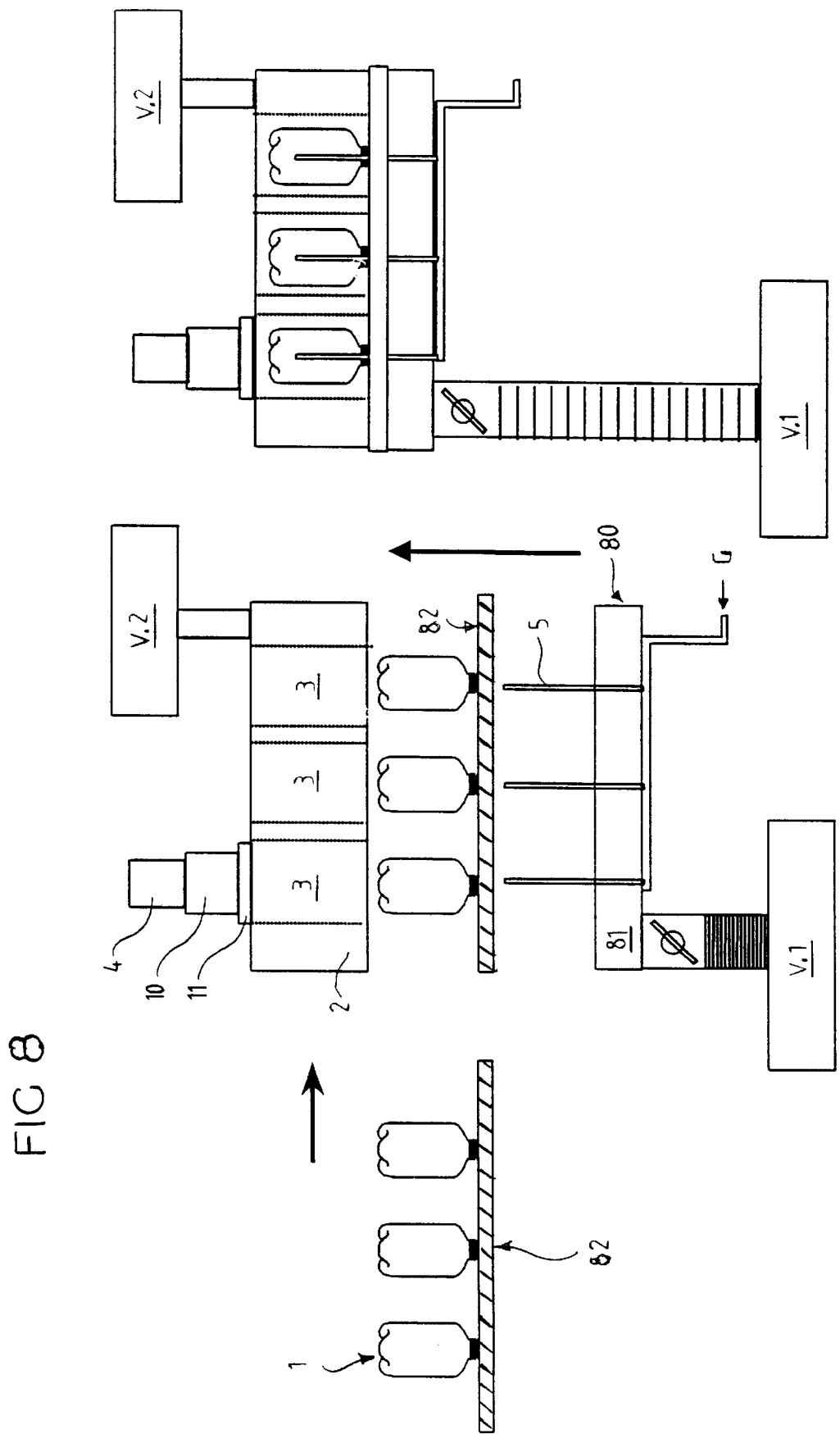
FIG. 8 shows schematically a further exemplified apparatus for plasma treating batches of bottles in an array of inventive one-bottle-apparatuses.

FIG. 8 shows a further exemplified apparatus for plasma treating batches of bottles in an array of inventive one-bottle-apparatuses. This array of one-bottle-apparatuses comprises a plurality of microwave confinements 3 each equipped as described with a microwave generator 4 and suitable coupling means 10/11, the microwave confinements being positioned in a common vacuum chamber 2 with a vacuum pump V.2 as described in connection with FIG. 5, whereby microwave confinements 3 and vacuum chamber 2 are closed by a neck plate 82. The array further comprises an arrangement 80 comprising a plenum 81 connected to a vacuum pump V.1 and having openings aligned with the axes of each microwave confinement 3 and being tightly connectable to bottle openings or corresponding openings in the neck plate 82 and an array of gas feed means 5 also aligned with the axes of the microwave confinements and connectable to a source of process gas G.

FIG. 8 shows from the left to the right three stages of a batchwise plasma treatment of bottles 1. Firstly (left side of the Figure), the batch of bottles is positioned on the neck plate 82, their axes aligned with the openings and the bottlenecks are fixed with suitable fixing means. Then (middle of the Figure), the neck plate 82 with the bottles 1 is positioned between the array of microwave confinements and the arrangement 80. Then (right side of the Figure) the neck plate 82 is raised for positioning the bottles 1 in the microwave confinements 3 and for closing the confinements 3 and the vacuum chamber 2. The arrangement 80 is also raised for positioning the gas feed tubes 5 in the bottles 1 and for connecting the openings of the plenum 81 with the bottle openings or with the openings in the neck plate 82.

Instead of using a vacuum chamber 2 containing the microwave confinements only and venting it for each change of batch or bottles, it is possible to use a larger vacuum chamber containing also the arrangement 80 and moving the neck plate with the bottles into the vacuum chamber and out of it via a vacuum lock, i.e. positioning the neck plate with the bottles into a prechamber connected to the vacuum chamber with a vacuum tight entrance door, evacuating the prechamber, opening the entrance door and moving the neck plate into the vacuum chamber. For removing the bottles after treatment, the vacuum chamber comprises an exit door and an evacuated after chamber, which afterchamber is vented for removing the neck plate with the treated bottles. The advantage of such an arrangement is the fact that the vacuum chamber does not need venting on batch change and that for this reason shorter cycle times will be achieved.

In all examples described above, the plasma treatment is a one step process being carried out using one process gas or one mixture of process gases. In the same way though, plasma processes comprising a plurality of steps can be carried out also. The only apparatus adaptation necessary for such a process is means for corresponding switching of the connection of the process gas feed means from a source of a first process gas to a source of a further process gas.

As already mentioned, one example of a plasma process for treating the inside surface of a bottle is coating this inside surface with an $SiO_x$ layer for improving the gas barrier properties of the bottle. Such deposition on a 500 ml PET bottle as available on the market carried out in an apparatus as described above using the following process parameters gives the following results:

| | |
|---|---|
| process pressure inside bottle | 0.2 mbar |
| process pressure outside bottle | 0.01 mbar |
| flow of hexamethyldisiloxane | 2 sccm |
| flow of oxygen | 16 sccm |
| applied microwave power | 150 W |
| process time | 12 s |

Oxygen permeation of treated bottle in comparison with untreated bottle (permeation measured on standard MOCON equipment):

| | |
|---|---|
| uncoated bottle | 0.050 0.0025 ccO$_2$/bottle/day/0.21 atm |
| coated bottle | 0.006 0.0025 ccO$_2$/bottle/day/0.21 atm |

This result represents an improvement in oxygen permeation by a factor of more than eight.

All modifications, alterations and changes coming within the spirit and scope of the invention as set forth in the appended claims are herein meant to be included.

What is claimed is:

1. A method for treating, in a plasma enhanced process, an inside surface of a plastic bottle (1), said plastic bottle having a substantially cylindrical body, a bottom portion on one end of the body and a shoulder and neck portion with a relatively narrow opening on the other end of the body, the process comprising the steps of simultaneously evacuating the inside of the bottle (1) and an area outside of the bottle, igniting and sustaining a plasma inside the bottle, providing means for feeding a process gas into the bottle (1), and flowing the process gas (G) via the feeding means and through the bottle for a predetermined process time, wherein the means for feeding the process gas into the bottle (1) is selected from the group consisting of a gas feed tube (5), which is positionable in the bottle (1), and a gas feed nozzle, which is positionable in the opening of the bottle, and wherein, following said predetermined process time, simultaneously venting the inside and the outside of the bottle, wherein, for carrying out the process steps, the bottle (1) is positioned substantially coaxially in a substantially cylindrical microwave confinement (3) whereby, for igniting and sustaining the plasma inside the bottle (1), microwaves are coupled to the microwave confinement (3) from one face of the confinement towards which the bottom portion of the bottle (1) is facing and whereby the microwave confinement (3) is excited in a TM mode of resonance.

2. The method according to claim 1, wherein the TM mode of resonance is a $TM_{01n}$ mode wherein n is one of 1, 2, 3 or 4.

3. The method according to claim 1, wherein the bottle (1) is stretch-blow-moulded in a blow mould (20) with the help of a stretching rod (22), said bottle is treated in the plasma enhanced process immediately after stretch-blow-moulding whereby the blow mould (20) is evacuated and microwaves are coupled into the blow mould (20) through a microwave window (10) in a face of the mould (20) and whereby the process gas (G) is fed into the bottle through the stretching rod (22) that also serves as the gas feed tube (5).

4. The method according to claim 3, wherein the stretching rod/gas feed tube (22/5) is positioned in a gas feed position for the plasma enhanced process wherein a distal end of the rod is spaced a distance from a bottom wall of the bottle (1).

5. The method according to claim 1, wherein the plasma enhanced process is a one or more step process whereby, in one of the steps, the inside surface of the plastic bottle is coated with a layer of $SiO_x$ for improving the gas barrier properties of the bottle.

6. The method according to claim 5, wherein oxygen permeation of the coated bottle is improved by a factor of approximately eight, as compared with the bottle in its uncoated state.

7. A method for treating, in a plasma enhanced process, an inside surface of a plastic bottle (1), said plastic bottle having a substantially cylindrical body, a bottom portion on one end of the body and a shoulder and neck portion with a relatively narrow opening on the other end of the body, the process comprising the steps of simultaneously evacuating the inside of the bottle (1) and an area outside of the bottle, igniting and sustaining a plasma inside the bottle, providing means for feeding a process gas into the bottle (1), and flowing the process gas (G) via the feeding means and through the bottle for a predetermined process time, wherein the means for feeding the process gas into the bottle (1) is selected from the group consisting of a gas feed tube (5), which is positionable in the bottle (1), and a gas feed nozzle, which is positionable in the opening of the bottle, wherein the bottle (1) is filled immediately after treatment in the plasma enhanced process whereby, instead of venting the inside of the bottle, a liquid (c) is drawn into the bottle following said predetermined process time, wherein, for carrying out the process steps, the bottle (1) is positioned substantially coaxially in a substantially cylindrical microwave confinement (3) whereby, for igniting and sustaining the plasma inside the bottle (1), microwaves are coupled to the microwave confinement (3) from one face of the confinement towards which the bottom portion of the bottle (1) is facing and whereby the microwave confinement (3) is excited in a TM mode of resonance.

8. An apparatus for treating, in a plasma enhanced process, an inside surface of a plastic bottle (1), the apparatus comprising a vacuum chamber (2), means for evacuating the vacuum chamber and an inside of the bottle (1) positioned in the vacuum chamber (2), means for igniting and sustaining a plasma inside the bottle and means for feeding a process gas (G) into the bottle, wherein the means for feeding a process gas into the bottle (1) is a gas feed tube (5) positionable in the bottle (1) or a gas feed nozzle positionable in the opening of the bottle, and wherein the apparatus further comprises a substantially cylindrical microwave confinement (3) into which confinement the bottle is positionable substantially coaxially and wherein the apparatus further comprises a microwave generator (4) and means for coupling the microwaves generated by the microwave generator (4) to the microwave confinement (3) from the one face towards which a bottom portion of the bottle is facing, whereby the microwave generator (4), the microwave coupling means and the microwave confinement (3) are designed and tuned for excitement of the microwave confinement in a TM mode.

9. The apparatus according to claim 8, wherein the means for coupling the microwaves to the microwave confinement (3) comprises a microwave window (10).

10. The apparatus according to claim 9, wherein the microwave confinement (3) is defined by a cylindrical part (3.1) inside the vacuum chamber (2) and by a neck plate (3.2) and an opposite plate (3.3), the neck and opposite plates (3.2 and 3.3) being parts of the vacuum chamber, (2) and wherein the opposite plate (3.3) comprises the window (10), which is transparent to microwaves.

11. The apparatus according to claim 8, wherein the microwave confinement (3) and the vacuum chamber (3) are in a cavity of a blow mould (20) of a stretch-blow-moulding apparatus, said mould (20) further comprises at least one channel (21) connectable to a vacuum source and a microwave-transparent window (10) in the area of the bottom portion, and wherein a stretching rod (22/5) of the stretch-blow-moulding apparatus is a hollow and perforated gas feed tube that is connectable to a process gas (G) source.

12. The apparatus according to claim 11, wherein the gas feed tube (5) is removable from the bottle (1) and the bottle opening is connectable to a source of a liquid (C) to be filled into the bottle.

13. The apparatus according to claim 8, wherein the apparatus is positioned within a line or matrix of similar apparatuses (50 to 61) which apparatuses have common vacuum sources (55, 57) and gas source (56).

14. The apparatus according to claim 13, wherein the matrix or line comprises a common vacuum chamber (71), in which the plurality of apparatuses are accommodated.

15. The apparatus according to claim 13, wherein the matrix or line comprises a vacuum plenum (81) extending over the whole area of the matrix or line and connected to a vacuum pump to which vacuum plenum (81) all necks of bottles to be treated are connectable.

* * * * *